(12) United States Patent
Erver et al.

(10) Patent No.: US 10,160,707 B2
(45) Date of Patent: Dec. 25, 2018

(54) PROCESS FOR PREPARING 3-CHLORO-2-VINYLPHENOL

(71) Applicant: Bayer CropScience Aktiengesellschaft, Monheim am Rhein (DE)

(72) Inventors: Florian Erver, Wiesbaden (DE); Mark James Ford, Wiesbaden-Breckenheim (DE)

(73) Assignee: Bayer CropScience Aktiengesellschaft, Monheim am Rhein (DE)

( * ) Notice: Subject to any disclaimer, the term of this patent is extended or adjusted under 35 U.S.C. 154(b) by 11 days.

(21) Appl. No.: 15/317,912

(22) PCT Filed: Jun. 8, 2015

(86) PCT No.: PCT/EP2015/062648
§ 371 (c)(1),
(2) Date: Dec. 9, 2016

(87) PCT Pub. No.: WO2015/189114
PCT Pub. Date: Dec. 17, 2015

(65) Prior Publication Data
US 2017/0101359 A1  Apr. 13, 2017

(30) Foreign Application Priority Data
Jun. 11, 2014  (EP) .................................. 14172039

(51) Int. Cl.
| C07C 37/06 | (2006.01) |
| C07C 303/28 | (2006.01) |
| C07C 309/66 | (2006.01) |
| C07C 309/73 | (2006.01) |
| C07C 39/373 | (2006.01) |
| A01N 31/08 | (2006.01) |

(52) U.S. Cl.
CPC .............. *C07C 37/06* (2013.01); *A01N 31/08* (2013.01); *C07C 303/28* (2013.01); *C07C 309/66* (2013.01); *C07C 309/73* (2013.01)

(58) Field of Classification Search
CPC ..... C07C 37/06; C07C 309/73; C07C 303/28; C07C 309/66
See application file for complete search history.

(56) References Cited

U.S. PATENT DOCUMENTS

| 2,183,574 A | 12/1939 | Levine et al. |
| 2,204,565 A * | 6/1940 | Britton ...................... C07C 1/30 585/359 |
| 2,210,563 A | 8/1940 | Adrussow et al. |
| 2,559,441 A | 7/1951 | Judd et al. |
| 2,694,079 A * | 11/1954 | Holysz .................... C07J 5/0053 552/544 |
| 2,725,404 A | 11/1955 | Montes et al. |
| 2,729,686 A | 1/1956 | Humphreys et al. |
| 2,742,508 A | 4/1956 | Johnson et al. |
| 2,745,883 A | 5/1956 | Jenney et al. |
| 2,773,105 A | 12/1956 | Kolka et al. |
| 2,980,721 A | 4/1961 | McMaster et al. |
| 4,576,935 A | 3/1986 | Schwarz et al. |
| 5,424,460 A * | 6/1995 | Duhamel ................ C07C 35/48 549/546 |
| 2010/0240619 A1 | 9/2010 | Gregory et al. |
| 2011/0224257 A1 | 9/2011 | Cristau et al. |

FOREIGN PATENT DOCUMENTS

| DE | 254473 | 11/1911 |
| DE | 824045 | 10/1951 |
| DE | 3239288 | 4/1984 |
| WO | WO-2009/094407 | 7/2009 |
| WO | WO 2012/025557 | 3/2012 |
| WO | WO-2014/206896 | 12/2014 |

OTHER PUBLICATIONS

Wright, D. et al., Ohio University "Lithium Carbonate." 1995 [online]: John Wiley & Sons, Ltd. [retrieved on Feb. 16, 2018]. Retrieved from <http://reag.paperplane.io/00001693.htm>. (Year: 1995).*
Kang et al. "Regarding a Generalized Scale of Solvent Polarities." J. Am. Chem. Soc. 1977, 99, 8325-8327. (Year: 1977).*
Germano, A. et al. (1954). "Additive chlorination of fluorobenzene," *Helvetica Chimica Acta* 37(156-157): 1343-1345.
Livar, M. et al. (1956). "Analytical rectification of technical trichlorobenzene combined with isolation of pure isomers," *Chemicke Zvesti* 10: 436-449.
Alvarez-Manzaneda, E. et al. (2007). "Novel synthetic strategy toward abietane and podocarpane-type diterpenes from ( − )-sclareol: synthesis of the antitumor (+)-7-deoxynimbidiol," *Tetrahedron Letters* 48:8930-8934.
Auret, B. J. et al. (Jan. 1, 1984). "Regioselective Dihydroarene Oxide Formation during ortho-Hydroxylation of Halogenobenzes by Fungi," *Journal of the Chemical Society, Perkin Transaction I*, pp. 2659-2664.
Batt, F. et al. (Nov. 17, 2007). "Unexpected tosyl deprotection during osmium catalyzed dihydroxylation," *Tetrahedron Letters* 49(3): 566-568.
De Buyck, L. et al. (1987). "Functionalization of Isophorone involving Polychlorination. Part II," *Bull. Soc. Chim. Belg.* 96(9): 663-674.
Extended European Search Report dated Sep. 11, 2014 for European Application No. 14172039.1 filed on Jun. 11, 2014, 7 pages.
Germano, A. et al. (1954). "Chloration additive du fluorobenzéne," *Helvetica Chimica Acta* 37(156-157): 1343-1345.
Greene, T. W. et al (Jan. 1, 1999). "Protective Groups in organic Synthesis Third Edition," *Protective Groups in organic Synthesis* Ed. 3:276-287, XP003001214.

(Continued)

*Primary Examiner* — Amanda L Aguirre
(74) *Attorney, Agent, or Firm* — Morrison & Foerster LLP

(57) ABSTRACT

The present invention describes a novel process for preparing 3-chloro-2-vinylphenol which, owing to the chemoselectivity achieved, also allows direct conversion into (3-chloro-2-vinylphenyl)methane-sulphonate.

7 Claims, No Drawings

(56) References Cited

OTHER PUBLICATIONS

International Search Report dated Jul. 23, 2015 for PCT Application No. PCT/EP2015/062648, filed on Jun. 8, 2015, 11 pages.
Kubátová, A. et al. (2002). "Dechlorination of Lindane, Dieldrin, Tetrachloroethane, Trichloroethene, and PVC in Subcritical Water," *Environmental Science & Technology* 36(6):1337-1343.
Livar, M. et al. (1956). "Analytická. Rektifikácia Technického Trichlórbenzénu Spojená S Izoláciou Čistých Izomérov," *Chemicke Zvesti* 10:436-449.
Majgier-Baranowska, H. et al (1998). "Synthesis of 4-hydroxyesrogens from steroid 4,5-epoxides: thermal rearragement of 4-chloro-4,5-epoxides." *Journal of the chemical Society, Perkin Transaction I*, pp. 1967-1972.
Mori, K. et al. (1982). "A General Synthetic Method for Prenylated Phends of Microbiol origin," *Tetrahedron* 38(9):1221-1225.
Prat, D. et al. (2013). "Sanofi's Solvent Selection Guide: A Step toward more sustainable Processes." *Organic Process Research & Development*, 17:1517-1525.
Ueno, S. et al (May 1, 2007). "Ruthenium-Catalized Carbon-Carbon Bond Formation via The Cleavage of an Unteactive Aryl Carbon-Nitrogen Bond in Aniline Derivatives with Organoboronates", *Journal of the American Chemical Society*, 129(19):6098-6099, XP 055134803.

\* cited by examiner

PROCESS FOR PREPARING 3-CHLORO-2-VINYLPHENOL

CROSS REFERENCE TO RELATED APPLICATIONS

This application is the national stage of International Application No. PCT/EP2015/062648, filed internationally on Jun. 8, 2015, which claims the benefit of European Application No. 14172039.1, filed Jun. 11, 2014, the disclosures of which are hereby incorporated by reference in their entireties for all purposes.

The present invention relates to a novel process for preparing 3-chloro-2-vinylphenol and salts thereof and the use of these for preparing pharmaceutical and agrochemical active compounds.

3-Chloro-2-vinylphenol derivatives are important precursors of pharmaceutical and agrochemical active compounds (c.f., for example, patent applications WO 2008/013622, WO 2009/094407, US 2010/0240619, US 2011/224257 and WO 2012/025557).

The synthesis of 3-chloro-2-vinylphenol is described in the patent US 1995/5424460. 1,5,5-Trichloro-6-vinyl-7-oxabicyclo[4.1.0]heptane is refluxed in N,N-dimethylformamide (DMF), forming 3-chloro-2-vinylphenol by elimination of two equivalents of hydrogen chloride. 1,5,5-Trichloro-6-vinyl-7-oxabicyclo[4.1.0]heptane is obtained by basic chlorination of cyclohexanone to give 2,2,6,6-tetrachlorocyclohexanone and subsequent addition of vinylmagnesium bromide and "in situ" cyclization to form the epoxide. This process has some significant disadvantages. Firstly, the reproduction-toxic DMF is used as solvent; according to the publication in *Org. Process. Res. Dev.* 2013, 17, 1517-1525, this may possibly no longer be allowed to be used for industrial syntheses in the future. From an economic point of view, too, this solvent is unsuitable because of the difficulty of separating it from the product and especially from aqueous wastes which generally have to be incinerated as such. In addition, the reaction is carried out under relatively energy-intensive conditions since a reaction temperature of 153° C. is necessary for the reaction. The hydrogen chloride liberated is also not neutralized, which at the given reaction temperature unavoidably contributes to partial decomposition of the solvent and to impairment of the chemoselectivity. The aromatization reaction leads to an only moderate yield of 75.5%. This is evidence of either an only moderate reaction selectivity or unsatisfactory product stability under the acidic conditions prevailing. This circumstance makes purification of the crude product absolutely necessary in this process. In addition, a purification by column chromatography as described in this patent is inconceivable for an agrochemical, industrial reaction.

However, compared to other processes known from the literature for eliminating hydrogen halides from substituted cyclohexanes to form unsaturated cyclohexanes or benzene derivatives by complete aromatization, the abovementioned process represents the present state of the art for preparing 2,3-substituted phenols selectively in the hitherto economically most advantageous way. As can be seen from the patents DE 1911/254473 and US 1939/2183574, inorganic catalysts such as calcium oxide or barium(II) chloride are required at temperatures of 300-500° C. for converting chlorocyclohexane into cyclohexene. According to the patents US 1940/2204565 and DE 1949/824045, the same transformation can be carried out at lower, but still high, temperatures of 200-300° C. when sodium hydroxide, calcium hydroxide, water or organic bases such as N-ethylcarbazole or dibenzopyrrole are used as catalysts. The double elimination of hydrogen bromide or hydrogen chloride from 1,2-dihalocyclohexane likewise requires, according to the patent US 1940/2210563, the presence of an inorganic catalyst such as aluminium oxide and methanol at temperatures of about 300° C. The aromatization of 1,2,3,4,5,6-hexa-chlorocyclohexane (lindane) by elimination of three equivalents of hydrogen chloride to form the corresponding isomeric compounds 1,2,3-, 1,2,4- or 1,3,5-trichlorobenzene likewise requires temperatures in the range 300-350° C. when using kieselguhr, iron (US 1956/2729686) or activated carbon (US 1956/2773105). The use of metal salts such as aluminium(III) chloride (US 1949/2559441; US 1956/2742508) or iron(III) chloride (US 1955/2725404) allows a reaction at lower temperatures in the range 160-300° C., while the use of organic or inorganic bases such as sodium hydroxide or sodium arylsulphonates (US 1956/2745883; *Chemicke Zvesti* 1956, 436-437) even makes a further lowering of the temperature to 100-200° C. possible. However, the reaction of lindane in water at 125-150° C. (*Environ. Sci. Technol.* 2002, 1337-1343) has been found not to be chemoselective and leads to the compounds 1,4-dichlorobenzene, 2,5-dichlorophenol and phenol. The presence of water under slightly alkaline conditions thus also leads to partial replacement of chlorine atoms. Furthermore, according to the literature reference *Helv. Chim. Act.* 1954, 1343-1345, the selective preparation of 1,3,4,5-tetra-chloro-2-fluorobenzene from the lindane derivative 1,1,2,3,4,5,6-heptachloro-4-fluorocyclohexane is possible by use of sodium methoxide in methanol, still at 210° C.

In contrast to cyclohexanes, which in the abovementioned examples have no carbonyl group, halogenated or unhalogenated phenols can be prepared from saturated or partially unsaturated cyclohexanones or cyclohexanediones under relatively mild conditions owing to the enolizability. For example, the reaction of 2,6-dichloro-3,5,5-trimethylcyclohex-2-en-1-one to form the isomeric compounds 2-chloro-3,4,5-trimethylphenol and 2-chloro-3,5,6-trimethylphenol can be successfully carried out in a yield of in each case 35% using DMA as solvent and the base triethylamine at 105° C. (*Bull. Soc. Chim. Belg.* 1987, 663-674). However, this is a relatively specific case in which the reaction does not proceed only via elimination of hydrogen chloride since a Meerwein rearrangement of one of the geminal methyl groups on a resonance-stabilized cation is required for product formation. In further reactions, the use of an organic base such as 1,8-diazabicyclo[5.4.0]undec-7-ene (DBU) in the case of dichlorinated cyclohexa-1,3-dione and a temperature of 66° C. in tetrahydrofuran (*Tetrahedron* 1982, 1221-1225) or in the case of a dichlorinated cyclohexanone and a temperature of 110° C. in toluene (*Tetrahedron Lett.* 2007, 8930-8934) is preferred for the elimination of hydrogen chloride to form the corresponding phenols. Although good yields are achieved, atom-uneconomical organic bases which are expensive both to procure and dispose of are unsuitable for an industrial synthesis, for which reason theses processes are ruled out. For this reason, the process for converting the halogenated epoxycyclohexane 3,4-dibromo-6-chloro-7-oxabicyclo[4.1.0]heptane into 2-chlorophenol in 51% yield by use of 1,5-diazabicyclo(4.3.0)non-5-ene (DBN) in tetrahydrofuran at 0° C. (*J. Chem. Soc.* 1984, 2659-2664) is not a feasible alternative. The thermal elimination (pyrolysis) of hydrogen chloride from a chlorinated epoxysteroid to form fused 1,2-dihydroxybenzene also gives a yield of only 22% at the quite high reaction temperature of 165° C. (*J. Chem. Soc.* 1998, 1967-1972).

A further comparison such as with the aromatization of halogenated quinone derivatives to form hydroquinones or further cyclohexanediones and cyclohexanetriones and also the aromatization of cyclohexan(on)es fused onto aromatic systems will be omitted at this point since said systems undergo aromatization even more readily and because of the product structures achieved are not comparable to the system discussed here.

Viewed in this way and taking account of the abovementioned disadvantages, only the patent US 1995/5424460 of Rhone Poulenc Chimie represents, owing to the comparatively easy availability of the raw material and the chemoselectivity achieved, the relevant prior art and the only usable approach to the development of an industrial synthesis of 3-chloro-2-vinylphenol.

In the light of the above-described prior art, it is an object of the present invention to provide a process which does not have the abovementioned disadvantages and thus allows access to 3-chloro-2-vinylphenol (I) in high yields.

The above-described object has been achieved by a process for preparing 3-chloro-2-vinylphenol of the formula (I),

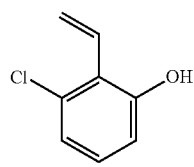

characterized in that 1,5,5-trichloro-6-vinyl-7-oxabicyclo[4.1.0]heptane of the formula (II),

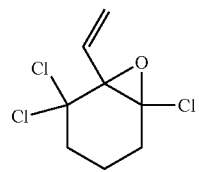

is reacted in the presence of a base, a dipolar aprotic additive and optionally a solvent to give the compound of the formula (I).

Surprisingly, the 3-chloro-2-vinylphenol of the formula (I) can be prepared in high purity, so that the process of the invention overcomes the abovementioned disadvantages of the preparative processes previously described in the prior art.

PROCESS DESCRIPTION

Scheme 1:

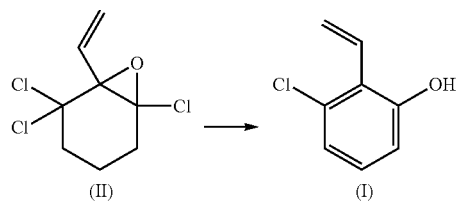

3-Chloro-2-vinylphenol (I) is prepared by reacting 1,5,5-trichloro-6-vinyl-7-oxabicyclo[4.1.0]heptane (II) in the presence of a base, a dipolar, aprotic additive and optionally a solvent.

Suitable dipolar aprotic additives are, for example, amides (e.g. N,N-dimethylformamide, N,N-dimethylacetamide, N-methylpyrrolidinone), carbonates (propylene carbonate, dimethyl carbonate, diethyl carbonate), nitriles (e.g. acetonitrile, propionitrile), sulphoxide/sulphones (e.g. dimethyl sulphoxide, sulpholane), ureas (N,N-dimethylpropyleneurea, N,N-dimethylethyleneurea) and carbamates (e.g. methyl N,N-dimethylcarbamate, ethyl N,N-dimethylcarbamate). Preferred additives are N,N-dimethylacetamide, propylene carbonate and sulpholane, with particular preference being given to N,N-dimethylacetamide.

Suitable solvents are ethers (e.g. methyl tert-butyl ether, tetrahydrofuran, 2-methyltetrahydrofuran, cyclopentyl methyl ether, 1,4-dioxane), aliphatics and aromatics (e.g. methylcyclohexane, n-heptane, toluene, chlorobenzene, xylene, mesitylene, 1,2-dichlorobenzene), esters (e.g. ethyl acetate, n-propyl acetate, i-propyl acetate, n-butyl acetate), alcohols (e.g. methanol, ethanol, n-propanol, i-propanol, n-butanol) or mixtures of these solvents mentioned. Preferred solvents are ethers and esters. Very particular preference is given to n-butyl acetate.

The reaction according to the invention is carried out either in the presence of a base and a dipolar aprotic additive or in the presence of a base, a dipolar aprotic additive and a solvent.

Preference is given to using a base and N,N-dimethylacetamide as additive.

Preference is also given to using a base, N,N-dimethylacetamide as additive and additionally a solvent.

Preference is also given to using a base, N,N-dimethylacetamide as additive and additionally n-butyl acetate as solvent.

Suitable bases are carbonates, (e.g. lithium carbonate, sodium carbonate, potassium carbonate and calcium carbonate), phosphates (e.g. potassium phosphate, sodium phosphate and lithium phosphate), carboxylates (e.g. potassium acetate, sodium acetate and lithium acetate, and also potassium formate, sodium formate and lithium formate), hydroxides (e.g. potassium hydroxide, sodium hydroxide and lithium hydroxide) and also organic bases (e.g. triethylamine, diethylisopropylamine, tri-n-butylamine, pyridine, picoline, lutidine and collidine). The bases are preferably used in stoichiometric amounts in order to take up exactly the amount of two equivalents of hydrogen chloride formed and constantly keep the pH neutral. The use of carbonates and organic bases is preferred. Particular preference is given to using lithium carbonate, sodium carbonate, potassium carbonate, calcium carbonate, triethylamine, diethylisopropylamine, tri-n-butylamine, pyridine, picoline, lutidine and collidine. Very particular preference is given to using triethylamine, tri-n-butylamine, calcium carbonate and lithium carbonate. The use of lithium carbonate is very particularly preferred.

A preferred embodiment of the process of the invention is as follows: the compound of the formula (II) is placed together with the additive and the base in an organic solvent in a reaction vessel and the reaction vessel is closed. The reaction mixture is subsequently heated while stirring well for a period of from 2 to 24 hours until the reaction is complete.

A very particularly preferred embodiment of the process of the invention is as follows: the compound of the formula (II) is placed together with N,N-dimethylacetamide and lithium carbonate in n-butyl acetate in a reaction vessel and the reaction vessel is closed. The reaction mixture is subsequently heated while stirring well for a period of from 2 to 48 hours until the reaction is complete.

The process of the invention is usually carried out at temperatures in the range from 50° C. to 150° C., preferably in the range from 110° C. to 130° C.

The process of the invention is carried out either under atmospheric pressure or at a pressure of up to 5 bar, depending on the solvent. It is preferably carried out at atmospheric pressure.

The work-up and isolation of the compound of the formula (I) is then carried out by cooling the reaction mixture to 15-35° C. and subsequently either filtering off the salts or by washing with deionized water. The organic phase is, if necessary, preferably dried azeotropically and the product is either reacted further in a solution to effect subsequent functionalization of the hydroxy group or isolated as an oil after removal of the solvent under reduced pressure.

The reaction time can vary greatly, in the range from a few minutes to some hours, depending on the solvent, the concentration and the external temperature applied.

The work-up and isolation of the compound of the formula (I) is generally carried out by cooling the reaction mixture to a temperature range from −20° C. to 25° C. After aqueous removal of the salts and the dipolar, aprotic additive, the compound of the formula (I) is isolated as an oil from the organic phase after removal of the solvent or extractant under reduced pressure.

If the compound of the formula (I) obtained in this way is provided with bases, the corresponding salts, viz. the phenoxides, are formed.

A further advantage of the process is that the compound of the formula (I) is prepared in a purity which allows a direct subsequent reaction without prior purification. For example, it is possible for 3-chloro-2-vinylphenol (I) to be reacted further in the solvent or extractant after an aqueous scrub and drying of the organic phase in an alkylation reaction as described in the patent US 2011/224257 (e.g. allylation, propargylation or 2-methoxyethylation) or else a sulphonation or acylation reaction,

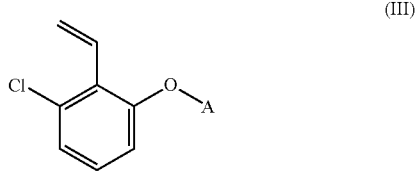

where
A is selected from among mesyl, tosyl, acyl, phosphonyl, phosphoryl.

In a preferred embodiment, the compound of the formula (I) is converted directly into the substance (3-chloro-2-vinylphenyl)methanesulphonate of the formula (III-I)

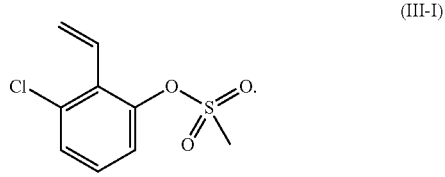

The compound of the formula (II) is known from US 1995/5424460.

The following example illustrates the process of the invention:

Preparation of 3-chloro-2-vinylphenol 15.00 g (80% purity, 52.7 mmol, 1.0 eq.) of 1,5,5-trichloro-6-vinyl-7-oxabicyclo[4.1.0]heptane and 4.70 g (52.7 mmol, 1.0 eq.) of lithium carbonate and 19.2 g of N,N-dimethylacetamide (220.5 mmol, 4.18 eq.) were placed in 28.8 g of n-butyl acetate (247.9 mmol, 4.7 eq.) in a reaction vessel and heated while stirring to an internal temperature of 125° C. (external temperature of 135° C.). After 8 hours, complete conversion of the starting material into 3-chloro-2-vinylphenol was detected by GC analysis. The suspension was then cooled to an internal temperature of 25° C. by removal of the heating bath and admixed with 25 ml of deionized water. The phases were subsequently separated and the organic phase was washed with 2×20 ml of half-concentrated sodium chloride solution and also 2×20 ml of deionized water. The organic phase was then freed of water and solvent under reduced pressure and the product was isolated as a yellow oil: yield 6.93 g (85% of theory) $^1$H-NMR (CDCl$_3$, 400 MHz) δ (ppm)=7.08 (dd, J=8.0, 8.0 Hz, 1H, H$_{5-Ar}$), 6.96 (d, J=8.0 Hz, 1H, H$_{4-Ar}$), 6.84 (d, J=8.0 Hz, 1H, H$_{6-Ar}$), 6.79 (dd, J=12.0, 12.0 Hz, 1H, H$_{c-Vin}$), 5.74 (d, J=12.0 Hz, 1H, H$_{b-Vin}$), 5.73 (s, 1H, OH), 5.68 (d, J=12.0 Hz, 1H, H$_{a-Vin}$).

The effect of various bases on the chemoselectivity and thus yield of the reaction which was otherwise carried out under identical conditions may be demonstrated by a few examples in the following table:

| Base | Yield |
|---|---|
| 1.0 equivalent of lithium carbonate | 85% |
| 1.0 equivalent of calcium carbonate | 84% |
| 1.0 equivalent of sodium carbonate | 73% |
| 1.0 equivalent of potassium carbonate | 62% |
| 2.0 equivalents of triethylamine | 84% |

Direct Preparation of (3-chloro-2-vinylphenyl)methanesulphonate Via 3-chloro-2-vinylphenol 15.00 g (80% purity, 52.7 mmol, 1.0 eq.) of 1,5,5-trichloro-6-vinyl-7-oxabicyclo[4.1.0]heptane and 4.70 g (52.7 mmol, 1.0 eq.) of lithium carbonate and 19.2 g of N,N-dimethylacetamide (220.5 mmol, 4.18 eq.) were placed in 28.8 g of n-butyl acetate (247.9 mmol, 4.7 eq.) in a reaction vessel and heated while stirring to an internal temperature of 125° C. (external temperature of 135° C.). After 8 hours, complete conversion of the starting material into 3-chloro-2-vinylphenol was detected by GC analysis. The suspension was then cooled to an internal temperature of 25° C. by removal of the heating bath and admixed with 25 ml of deionized water. The phases were subsequently separated and the organic phase was washed with 2×20 ml of half-concentrated sodium chloride solution and 2×20 ml of deionized water. The organic phase was then dried azeotropically under reduced pressure and a small amount of solvent was distilled off. The distillation residue was subsequently admixed with 5.90 g (58.28 mmol, 1.3 eq.) of triethylamine, cooled to 0° C. and 6.67 g (58.28 mmol, 1.3 eq.) of methanesulphonyl chloride was introduced into the reaction solution over a period of 15 minutes. After the addition was complete, the mixture was heated to 22° C. and the suspension was admixed with 50 ml of deionized water. The phases were subsequently separated, the aqueous phase was extracted with 25 ml of n-butyl acetate and the combined, organic phases were washed with 50 ml of deionized water. Remaining water and a major part of the solvent were subsequently distilled off from the organic phase. Digestion with n-heptane and subsequent cooling to −20° C. made it possible to obtain the target compound as a light-yellow solid by crystallization, filtration and drying. Yield 8.71 g (71% of theory over two stages), $^1$H-NMR (CDCl$_3$, 400 MHz) δ (ppm)=7.36 (dd, J=8.0, 1.2 Hz, 1H, H$_{4-Ar}$), 7.34 (dd, J=8.0, 1.2 Hz, 1H, H$_{2-Ar}$), 7.23 (dd, J=8.0, 1.2 Hz, 1H, H$_{3-Ar}$), 6.80 (dd, J=18.0, 12.0 Hz, 1H, H$_{c-Vin}$), 5.92 (dd, J=18.0, 1.6 Hz, 1H, H$_{b-Vin}$), 5.74 (dd, J=12.0, 1.6 Hz, 1H, H$_{a-Vin}$), 3.12 (s, 3H, OSO$_2$CH$_3$).

The invention claimed is:

1. A process for preparing a compound of formula (I),

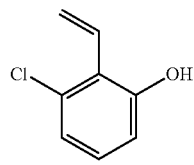

(I)

comprising reacting a compound of formula (II),

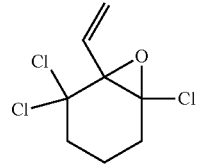

(II)

with a base selected from the group consisting of lithium carbonate, sodium carbonate, potassium carbonate, calcium carbonate, triethylamine, diethylisopropylamine, tri-n-butylamine, pyridine, picoline, lutidine, and collidine; and N,N-dimethylacetamide as a dipolar aprotic additive; and optionally in the presence of a solvent selected from the group consisting of methyl tert-butyl ether, tetrahydrofuran, 2-methyltetrahydrofuran, cyclopentyl methyl ether, 1,4-dioxane, ethyl acetate, n-propyl acetate, i-propyl acetate, and n-butyl acetate, to give the compound of formula (I).

2. The process according to claim 1, wherein the base is triethylamine, tri-n-butylamine, calcium carbonate, or lithium carbonate.

3. The process according to claim 1, wherein the base is lithium carbonate.

4. The process according to claim 1, wherein a solvent is used.

5. The process according to claim 4, wherein the solvent is n-butyl acetate.

6. The process according to claim 4, wherein the compound of formula (I) is not isolated but instead is directly converted further into a compound of formula (III)

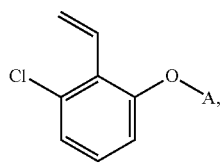

(III)

wherein A is selected from the group consisting of mesyl, tosyl, acyl, phosphonyl, and phosphoryl;

using a base and a reagent Q-A, wherein Q is selected from the group consisting of chloride and bromide.

7. The process according to claim 6, wherein Q is chloride and A is mesyl.

* * * * *